May 25, 1965 H. C. BROWNELL Plant Pat. 2,521
ROSE PLANT
Filed Dec. 17, 1963
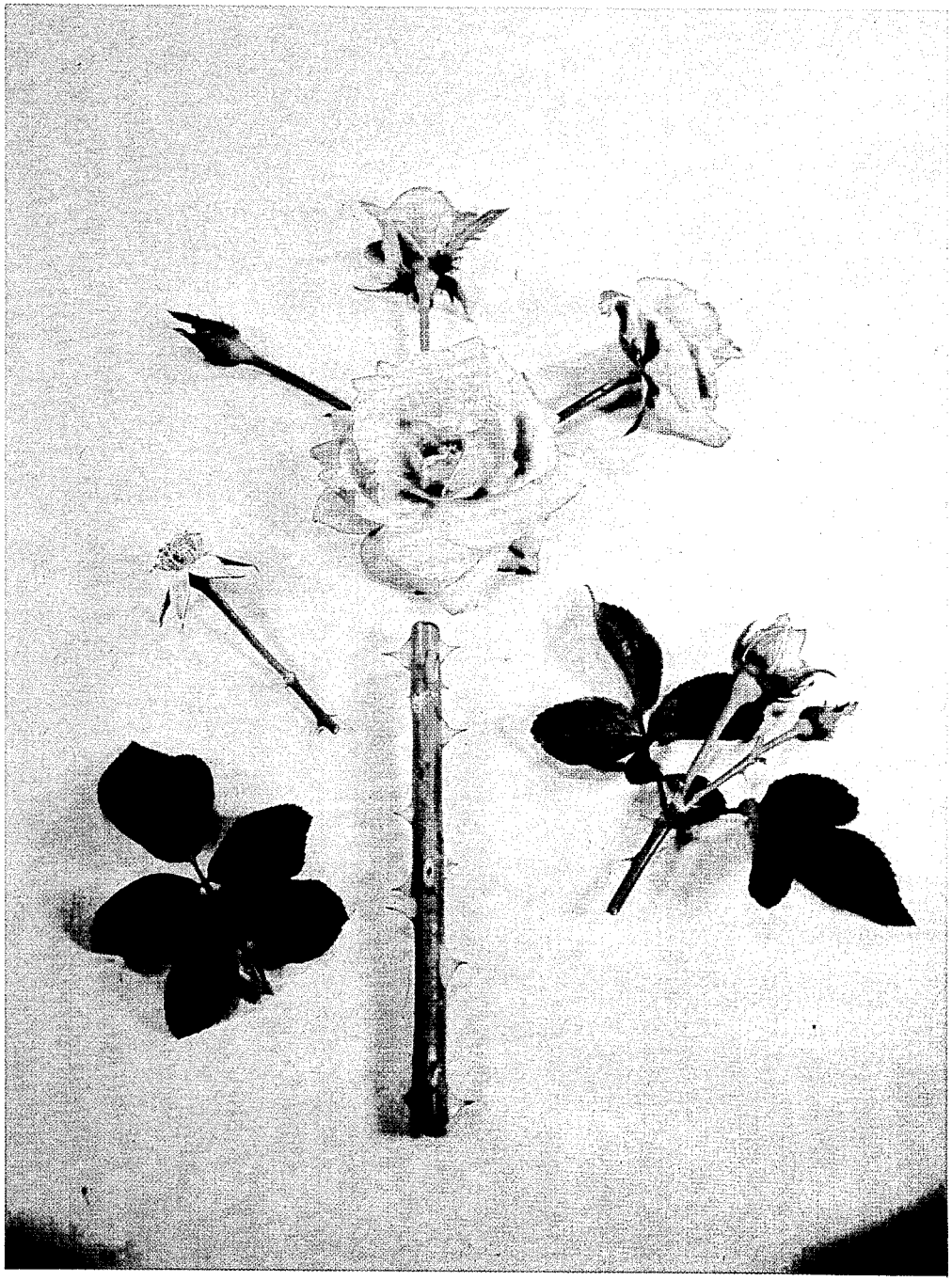
Inventor
Herbert C Brownell United States Patent Office Plant Pat. 2,521
Patented May 25, 1965

2,521
ROSE PLANT
Herbert C. Brownell, Little Compton, R.I.
Filed Dec. 17, 1963, Ser. No. 331,330
1 Claim. (Cl. Plt.—19)

My invention relates to roses and especially to a new, original and distinct variety of the class known commercially as "hybrid tea" and is a variant in that class, being a *Rosa wichuraiana* hybrid tea hybrid, produced by me and under my direction in the breeding grounds of my research gardens in Little Compton, Rhode Island, by selection of variety variations and by cross pollination, which new rose plant can be and has been asexually reproduced.

My new rose plant is new as to the following characteristics and especially as to their joint association with the characteristics inherited from *Rosa wichuraiana,* of hardiness, or immunity from serious injury on account of cold temperatures prevailing in certain parts of the Northern United States.

The deep pink color (ordinary dictionary definition) of its petals in combination with the unique brilliance thereof and their tendency to hold these colors under exposure, fading only very slightly under direct rays of the sun.

The novelty and variation within certain definite limits of the form of the bloom, the recurl of the petals as the flower opens, its character of holding its form for a long time and the petalage of the flowers;

Its unusual abundance of flowers, at bloom time and after early bloom time until frost;

Its character of ascending in height by recurrent branching and progressively longer stems from the base;

The character of producing many seven leafleated leaves, which character seldom has obtained on hybrid teas not having *Rosa wichuraiana* ancestry;

And especially its characteristic of freedom from premature defoliation by blackspot, under certain definite conditions of exposure, without any cultural control.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; outdoor; seedling; for cut flowers and garden decoration.
Class: Hybrid tea.
Breeding: Seedling.
*Seed parent.*—Pink Princess—Plant Patent Number 459.
*Pollen parent.*—Queen Elizabeth—Plant Patent Number 1,259.
Propagation: Holds its distinguishing characteristics through succeeding propagations by budding.

*Flower*

Locality where grown and observed: Little Compton, Rhode Island, U.S.A.
Flowers borne: Singly and in clusters on stems of medium length and normal strength.
Quantity of bloom: Abundant, outdoors.
Continuity: Continuous during growing season until frost.
Fragrance: From none to slight.
Bud:
*Peduncle.*—Average length; medium caliper; moderate number of red hairs. Color—Oxblood Red, Plate 00823/3.

*Before calyx breaks.*—Size—medium. Form—globular; with slender foliaceous parts extending beyond the tip of the bud equal to ½ or more of its length. Color—Fern Green 0862/1 overlaid with Garnet Brown 00918.
*As calyx breaks.*—Color (outside of petal)—Ruby Red 827.
*As first petal opens.*—Size—medium. Form—globular. Color: outside—Cardinal Red 822; inside—Rose Red 724.
*Opening.*—Opens up well.
Bloom:
*Size (when fully open).*—Medium large; from 3½ inches to 4 inches.
*Petalage.*—Double; from 35 to 50 petals; arranged regularly.
*Form.*—Globular, becoming cupped. Petals recurl as bloom opens.
Petals:
*Texture.*—Thick; leathery; inside and outside satiny.
*Shape.*—Orbiculate; no notches.

This description of a newly opened flower was made from a rose grown outdoors at Little Compton, Rhode Island in the month of September.

*Color.*—Outer petal: outside surface—Rose Opal 022; inside surface—Spiraea Red 025. Inner petal: outside surface—Spiraea Red 025/1; inside surface—Spiraea Red 025/1. At base of petal a small section Chinese Yellow 606.

This description was made from a rose open for 3 days outdoors in the month of September at Little Compton, Rhode Island.

*Color.*—Outer petal: outside surface—Rose Red 724; inside surface—Rose Red 724/2. Inner petal: outside surface—China Rose 024/2; inside surface—China Rose 024/1.
*Flower longevity.*—On bush in garden 5 or 6 days in September. Cut roses grown outdoors and kept at living room temperature 3 or 4 days in September.

*Reproductive Organs*

Stamens: Average number; arranged slightly irregular.
Filaments: Medium number; most with anthers; medium length. Color—Indian Yellow 6.
Anthers: All open at once; medium sized. Color—Maize Yellow 607.
Pollen: Abundant. Color—Spanish Orange 010.
Pistils: Many.
Styles: Uneven; medium length; from thin to average caliper. Color—near Amber Yellow 505/3.
Stigma: Color—Amber Yellow 505/1.
Ovaries: Usually all enclosed in calyx.
Hips: Short; globular; smooth. Color (mature)—Pod Green 061.
Sepals: Permanent; long pointed. Color: outside—Scheele's Green 860/1; inside—Lavender Green 000761/1.
Seeds: Abundant; from 25 to 30 per hip. Usually small to medium size.

*Plant*

Foliage:
*Leaves.*—Compound of usually 3 to 7 leaflets; normal quantity; small to medium size.
*Leaflets.*—Shape—ovate; pointed apex. Base—round. Margin—simply serrate.
*Color.*—Mature: upper surface—Ivy Green 0001060/1; under surface—Sage Green 000861/1. Young: upper surface—Ivy Green 0001060/2; under surface—Lavender Green 000761.
*Rachis (the supporting stem of the compound leaf).*—Slightly smaller than average size. Upper side— grooved, with numerous stipitate glands on edges. Under side—smooth with two to four small prickles.

*Stipules.*—Short to medium; average width; with points from short to medium length, the upper of which normally form an angle of about 90 degrees.

*Disease resistance.*—Better-than-average resistance to blackspot and mildew as compared with other varieties grown under comparable conditions at Little Compton, Rhode Island, and reported the same condition at Tyler, Texas.

Growth:

*Habit.*—Bushy; upright-spreading; much-branched.

*Growth.*—From very free to vigorous.

*Canes.*—Medium caliper.

*Main stems.*—Color—Spinach Green 0960/2 with overlay of Cardinal Red 822/1. Medium prickles—several; short; hooked slightly downward. Color—near Garnet Brown 00918/3. Hairs—none.

*Branches.*—Color—Lettuce Green 861/1 with overlay of Cardinal Red 882/1. Medium prickles—several; short; hooked slightly downward; color—Cardinal Red 822/1. Hairs—none.

*New shoots.*—Color—Ruby Red 827. Prickles—several; same color as new shoots. Hairs—none.

I claim:

A new and distinct variety of rose plant of the hybrid tea type, substantially as herein shown and described, characterized particularly as to novelty by its vigorous habit of growth, abundant foliage, its resistance to mildew and blackspot, and its ability to withstand moderate subzero temperatures in combination with its hybrid tea character and its *Rosa wichuraiana* ancestry.

No references cited.

ABRAHAM G. STONE, *Primary Examiner.*